(12) United States Patent
Kotov (10) Patent No.: US 6,689,338 B2
(45) Date of Patent: Feb. 10, 2004

(54) BIOCONJUGATES OF NANOPARTICLES AS RADIOPHARMACEUTICALS

(75) Inventor: Nicholas A. Kotov, Stillwater, OK (US)

(73) Assignee: The Board of Regents for Oklahoma State University, Stillwater, OK (US)

( * ) Notice: Subject to any disclaimer, the term of this patent is extended or adjusted under 35 U.S.C. 154(b) by 0 days.

(21) Appl. No.: 09/871,166

(22) Filed: May 31, 2001

(65) Prior Publication Data

US 2002/0015679 A1 Feb. 7, 2002

Related U.S. Application Data (60) Provisional application No. 60/208,631, filed on Jun. 1, 2000.

(51) Int. Cl.[7] ........................ A61K 51/00; A61K 33/38; A61K 33/34; A61M 36/14; A61N 59/16; A61N 59/20
(52) U.S. Cl. ...................... 424/1.69; 424/618; 424/637; 424/646; 424/654; 424/706
(58) Field of Search .............................. 424/1.65, 1.69, 424/9.32, 9.322, 2, 646, 654, 618, 637, 706

(56) References Cited

U.S. PATENT DOCUMENTS

| | | | |
|---|---|---|---|
| 5,427,767 A | 6/1995 | Kresse et al. ............... 424/9.32 |
| 5,990,479 A | 11/1999 | Weiss et al. ................. 250/307 |
| 6,048,515 A | * 4/2000 | Kresse et al. ............ 424/9.322 |
| 6,114,038 A | * 9/2000 | Castro et al. .......... 428/402.24 |
| 6,207,392 B1 | * 3/2001 | Weiss et al. .................. 435/7.1 |
| 6,235,540 B1 | * 5/2001 | Siiman et al. ............... 436/518 |
| 6,261,779 B1 | * 7/2001 | Barbera-Guillem et al. ... 435/6 |
| 6,274,323 B1 | * 8/2001 | Bruchez et al. ................. 435/6 |
| 6,333,110 B1 | * 12/2001 | Barbera-Guillem .... 428/402.24 |
| 6,350,515 B1 | * 2/2002 | Lawton et al. .............. 428/323 |
| 6,361,944 B1 | * 3/2002 | Mirkin et al. ................... 435/6 |
| 6,495,324 B1 | 12/2002 | Mirkin et al. ................... 435/6 |

FOREIGN PATENT DOCUMENTS

| | | | | |
|---|---|---|---|---|
| WO | WO 00/17655 A1 | 3/2000 | .......... G01N/33/58 |
| WO | WO 00/17656 A1 | 3/2000 | .......... G01N/33/58 |
| WO | WO 00/17103 A2 A3 | 3/2000 | .......... C01B/33/00 |
| WO | WO 00/17642 A2 A3 | 3/2000 | .......... G01N/33/53 |
| WO | WO 01/19405 A2 | 3/2001 | .......... A61K/47/48 |
| WO | WO 01/33223 A1 | 5/2001 | .......... G01N/33/543 |

OTHER PUBLICATIONS

Tiefenauer et al. "Antibody–magnetite nanoparticles: In vitro characterization of a potential tumor specific contrast agent for MRI", Bioconjugate Chem. (1993), 4(5), 347–52.*
PCT International Preliminary Examination Report for PCT/US01/17658, May 13, 2003.
XP–001006052: Schaertl, Sabine et al. A Novel and Robust Homogeneous Fluorescence–Based Assay Using Nanoparticles for Pharmaceutical Screening and Diagnostics. *Journal of Biomolecular Screening*, vol. 5, No. 4, pp. 227–237, 2000.
XP–002908597: Shiju, Hiroshi et al. Development of a cancer vaccine: peptides, proteins, and DNA. *Cancer Chemother Pharmacol.* 46 (Suppl), pp. S77–S82, 2000.

* cited by examiner

*Primary Examiner*—Sreeni Padmanabhan
*Assistant Examiner*—Lauren Q. Wells
(74) *Attorney, Agent, or Firm*—Fellers, Snider, Blankenship, Bailey & Tippens, P.C.

(57) ABSTRACT

A bioconjugate including a nanoparticle covalently linked to a biological vector molecule. The nanoparticle is a generally radioactive metal ion and most typically a metal sulfide or metal oxide. The biological vector molecule is typically a monoclonal antibody or fragment of a monoclonal antibody or a peptide having a known affinity to cancer cells. One or more additional, different biological moieties may be covalently linked to the nanoparticle in addition to the biological vector molecule to enhance its activity. The bioconjugate of the present invention has utility as an effective radiopharmaceutical to deliver a radiolabel in tumor treatment.

11 Claims, 3 Drawing Sheets

BIOCONJUGATES OF NANOPARTICLES AS RADIOPHARMACEUTICALS

CROSS REFERENCE TO RELATED APPLICATIONS

This invention claims benefit of copending United States Provisional Application Ser. No. 60/208,631 filed Jun. 1, 2000.

STATEMENT REGARDING FEDERALLY SPONSORED RESEARCH

The development of the subject matter of this application was partially supported by a grant from the National Science Foundation (NSF-EDS-9876265). Accordingly, the U.S. government may have rights in this invention.

BACKGROUND OF THE INVENTION

1. Field of the Invention

This invention relates generally to the effective diagnosis and treatment of cancer patients and, more specifically, to radiopharmaceuticals for use in connection with radioimmunotherapy and radioimmunodection.

2. Background

Effective treatment of cancer patients by using radioimmunotherapy (RAIT) and diagnostics of malignant tumors by radioimmunodetection (RAID) requires drastic improvement of tumor-to-background (T/B) distribution of a radiolabel. T/B ratio is the principal parameter that determines tumoricidal action, sensitivity of tumor detection and, most importantly, systemic toxicity of the compound. Radioactive isotopes of metals are used very often in various modalities of RAIT and RAID in the form of conjugates with monoclonal antibodies (mAbs).

Attachment of the radioisotope to the targeting molecule is the most important part of the preparation of the radioconjugate. In some cases, a direct approach to radiolabeling of antibodies with therapeutic radionuclides can be adopted by reducing internal disulfide bonds within the antibody and allowing, for example, technetium or rhenium ions to react directly with the resultant sulfhydryl groups. However, labeling strategies usually rely on the utilization of a multidentate ligand capable of selective chelation of the desired radionuclide. In order to avoid the release of the metal ion in the circulation and inevitable radiation injuries to healthy organs, metal ions must be strongly complexed by a chelating agent.

Ideally, the chelated nuclide would be rapidly excreted via the urinary tract without intracellular retention, with intact conjugate accumulating and being retained selectively at the tumor site. This is however clearly not always the case, and in several instances, persistent and unwanted retention of metallic nuclides has been reported. As the in vivo behavior of a given nuclide-chelator complex cannot be predicted easily, the choice of potential multidentate ligands is guided by conventional chelation chemistry. Macrocyclic multidentate ligands which provide the highest thermodynamic stability of the complex are frequently used for preparation of immunoconjugates. The typical examples of chelating agents are diethylenetriaminepentaacetic anhydride (DTPA), (diethylenetriaminetetraacetic acid (DTTA), (1,4,7,10-tetraazacyclododecane-N,N=,N⇒, N⇒=-tetraacetic acid) (DOTA), ethylenediaminetetra (methylene phosphonate) (EDTMP), 1,1-hydroxyethylidine diphosphonate(HEDP) and derivatives thereof. For preparation of conjugated structures they are frequently functionalized in one of the side chains by —$C_6H_4$—NCS or other groups to form a covalent bond with proteins.

Entrapment of metal ion into a framework of muldidentate poly (amino carboxylates) such as DOTA, DTPA covalently attached to mAbs has been proven to provide thermodynamically stable compounds suitable for clinical trials. Nevertheless, results obtained for human patients and for animal models indicate that the applicability of these compounds is limited by the high level of radioactivity in blood, bone marrow, kidney and liver. This necessitates reduction of in-vivo decomplexation of metal ions and strengthening radiolabel-mAb bond.

The tumor uptake and overall biodistribution of the radiolabeled compound depends on the metabolism of the mAb and the strength of radionuclide-antibody link. Although there is a substantial room for improving targeting properties of mAbs, all studies indicate that the thermodynamic and kinetic stability of the chelate in vivo of is of primary importance for the design of clinically successful radiochemicals.

The equilibrium constant of chelation for the best chelates used in RAIT and RAID is comparable to that for some proteins present in blood. Therefore, chelates are inherently prone to slow exchange of radioactivity with tumor-indifferent proteins. When radiopharmaceuticals are administered intravenously, they encounter endogenous metal-binding proteins such as albumin in concentrations 100–1000-fold greater than that of the radiopharmaceutical. Loss of radiometal to serum proteins leads to accumulation of radioactivity in normal tissues, especially liver, spleen, and kidney, reducing the radioactivity available for tumor uptake. Stability of the radioimmunoconjugate is a critically important factor in determining its usefulness for in vivo applications. This fact was experimentally established for the majority of radionuclides.

For complexes of $^{111}$In and bleomycin, partial dissociation of the ion from bleomycin caused severe bone marrow toxicity and increased the background γ-radiation significantly impairing its therapeutic and imaging capabilities. The tumor-to-background ratio varied from 1.0 to 2.9. Even for one of the most widely used and the strongest $^{111}$In chelate with octadentate ligand DTPA ($K_{diss}$=28.5) a high liver background has been observed. Most researchers agree that chelate instability is the primary reason for various immune mechanisms which contribute to accumulation of the radioactivity in non target organs. Recent study clearly indicate the direct dependence between the thermodynamic stability of various chelates (NTA, EGTA, EDTA, DTPA) bound to the B72.3 antibody and the tissue distribution and accumulated activity in blood and kidney.

Retention of $^{111}$In in normal tissues has been the major limitation in RAID applications. Improved clearance of $^{111}$In from liver tissue correlated with the strength of a labile linkage between the antibody and the chelator and with the structure of the chelator to provide for higher stability under in vivo conditions.

The loss of metal ion in circulation greatly limits the utilization of potent radionuclides with convenient energy and half-life characteristics such as [212]Pb. The short decay of [212]Pb time (10.6 hours, β, 0.57 and 0.33 MeV) permits rapid clearance from the system. When conjugated to specific mAb 103 A, [212]Pb-DOTA chelate was very efficacious at eliminating the tumor even in mice with large tumor burdens. However, due to lower pH values found in cells in which catabolism occurs, [212]Pb escapes the chelator and is taken up in bone and marrow. Bone marrow toxicity in this case was so high that accumulation of $^{212}$Pb in bones was dose limiting and lethal. Loss of the specificity of radiometal deposition was observed for $^{46}$Sc, $^{67}$Ga, and $^{90}$Y when the ion was not strongly chelated to its ligand.

Incorporation of a radiometal label into the protein structure by using nitrogen and sulfur atoms of aminoacids (NS systems) is very popular for technetium and rhenium. Comparative stability of these chelates is quite high. Importantly, metal species can be incorporated in an anionic form that makes recomplexation by native proteins less probable. Nevertheless, $^{188}$Re-labeled mAbs were found to be a marginal agent for controlling tumor growth. The failure of $^{188}$Re-IgG in some tumor models may be related to the combination of apparent instability of the labeled product and its short physical half-life. Interestingly the dissociation of $^{188}$Re from the protein occurred more quickly that for other isotopes such as $^{88}$Y. The release of rhenium is likely to be assisted by reoxydation of the chelate to $ReO_4^-$ by dissolved oxygen.

Importantly, for yttrium ($^{90}$Y, $^{88}$Y), lead ($^{212}$Pb) and samarium ($^{153}$Sm) the strength of the chelates must be particularly high. In ionic form these metals are capable of replacing $Ca^{2+}$ ions from bone, which halts excretion of the radionuclide and causes augmented radiation damage to healthy tissues.

The nature of medical applications imposes multiple requirements on the chemical characteristics of a potential chelating ligand. It has to be (a) strong (multidentate) complexing agent for the metal ion, (b) hydrophilic to afford solubility in water, (c) nontoxic, (d) capable of incorporating into a protein structure without causing its denaturation. For virtually every single radionuclide one has to design a special chelating system. For example macrocyclic bifunctional chelating agents, in particular, DOTA, derivatives incorporating yttrium-90 and indium-111 have shown excellent kinetic stability under physiological conditions. However, the slow formation of yttrium-DOTA complexes presents a technical problem that can lead to low radiolabeling yields unless conditions are carefully controlled.

The most successful chelating agents for preparation of radioconjugates are the products of a complex organic synthesis. Quite representative examples of a synthetic procedure can be found in Brechbiel, M. W.; Gansow, O. A.; Atcher, R. W.; Schlom, J.; Esteban, J.; Simpson, D. E.; Colcher, D., Synthesis of 1-(P-isothiocyanatobenzyl) Derivatives of DTPA and EDTA. Antibody Labeling and Tumor Imaging Studies, *Inorg. Chem.*, 1986, 25, 2772–2781. They consist of more than 6 consecutive steps. Synthetic sophistication not only increases the cost of the drug but also compromises the quality of the pharmaceutical by restricting how the label can be attached to mAb. Direct binding used for $^{99m}$Tc and $^{186}$Re without specilly designed chelating agents simplifies the procedure. However, it cannot be applied for other metals and may induce conformational changes in mAb or its fragments.

Entrapment of a metal ion into a framework of multidentate complex yields a thermodynamically stable structure, but quite often, is slow to form. Typically, incorporation of a radioactive ion takes >3 hours. The fast forming chelates like those of EDTA, undergo rapid transchelation to blood proteins. Slow kinetics of metal incorporation decreases the overall activity of short half-life radionuclides and necessitates removal of unbound radioactive species.

It is thus an object of the present invention to provide a new method of preparation of radioimmunoconjugates to obtain more stable agents for radiotherapy and diagnostics.

SUMMARY OF THE INVENTION

In accordance with the present invention metal chelates are replaced with small (2–5 nm in diameter) clusters of metal sulfide nanoparticles bound to mAbs or other biological molecules via a bifunctional organic stabilizer. The core materials of the nanoparticles, i.e. transition metal sulfides, are virtually insoluble in aqueous solutions due to partially covalent character of the crystal lattice. Negligible concentration of ionic species prevents transchelation in serum and release of radioisotopes in circulation.

Nanoparticles (NPs) combine properties of bulk solids and relatively large molecules. The core of NPs is made of inorganic material and retains some physical and chemical properties of its bulk predecessor, while the solubility and chemical reactivity is determined by a thin, virtually monomolecular layer, of organic molecules adsorbed to NP. This layer passivates the surface of the solid and protects the NP from further growth. A chemical compound forming this layer is often referred to as a stabilizer. The inorganic core may contain 100 to 10,000 atoms depending on its diameter (1–10 nm). The size can be accurately assessed by the position of UV absorption peak that was shown to shift to shorter wavelengths for smaller NPs due to size-quantization effect. Very small size, uniformity of particles, and critical role of the surface distinguishes NPs from both colloidal and molecular systems.

Although a large variety of materials can be prepared in this form, predominantly metal sulfides and oxides have been studied for preparation of NPs. Organic thiols, R-SH are known to be excellent stabilizers for these materials due to formation of a relatively strong covalent R-S-M link, where M stands for metal atom on the surface of nanoparticle. Numerous methods have been proposed for preparation of NPs in solid and liquid media, as well as at interfaces. See, Fendler, J. H. Membrane-mimetic Approach to Advanced Materials. Advances in Polymer Science. Vol. 113. Springer-Verlag: Berlin, 1994; C. Luagdilok and D. Meisel, Size Control and Surface Modification of Colloidal Semiconductor Particles, *Is. J. Chem,* 1993, 33, 53; P. V. Kamat, Interfacial Charge Transfer Processes in Colloidal Semiconductor Systems, *Prog. Reaction Kinetics,* 1994, 19, 277. By choosing an appropriate stabilizer and reaction conditions one can alter the diameter of the core with a precision of a few Angstroms.

Unique properties of NPs, i.e. their intermediate position between single molecule and a bulk compound, have made them excellent candidates for various applications. So far, scientists viewed them as perspective candidates for optical and electronic devices, while medical applications of inorganic nanoparticles are very limited.

The term nanoparticle appears in medical literature quite often. In most cases it is used to describe objects of from 30 to 300 nm in diameter represented by vesicles, polymers or colloids. These species are used for drug delivery and for diagnostic purposes. Confusion of terms used in different fields of chemistry should not obscure the fundamental difference that drug delivery agents are expected to remain in the blood stream for relatively long time while the radioimmunoconjugates must have a rapid blood clearance which is hardly achievable with large species 50–300 nm in diameter. Accordingly, it is contemplated that the term nanoparticles in the present invention includes particles of a smaller diameter.

The use of inorganic clusters in the nanometer region has been limited so far to conjugates of $Fe_3O_4$ magnetic clusters proposed for MRJ contrast agents. Ideologically, these are the assemblies that are quite similar to MPC: a mAb or other targeting compound attached to the magnetic core causes magnetic material to accumulate in tumor tissue, which increases the contrast of MRI images. Magnetic conjugates were proven to be quite efficient agents for MRI. From chemical point of view, synthetic approaches must be entirely different because of difficulty of covalent modification of oxide surfaces used in magnetic imaging. $Fe_2O_3$ and $Fe_3O_4$ nanoparticles and coating material (polyelectrolytes) are held together mostly by electrostatic forces. Metal sulfides offer a possibility to form stronger and more precisely organized assemblies via covalent bonds. Importantly, the requirements to chemical stability in radioimmunoconjugates is substantially stricter than in magnetic imaging because of the high toxicity of radioactive materials.

Here and later, the term "solution" shall be used rather than "dispersion" to describe nanoparticles in liquid media in order to emphasize the similarity with true molecular solutions. For nanoclusters 1–10 nm in diameter it is not only a valid but also a more appropriate terminology in accord with their chemical properties quite different from the common colloidal dispersions.

In connection with the present invention, instead of a multidentate ligand with a radioactive ion in the middle a radioactive nanoparticle is covalently linked to a biological vector molecule such as mAb, its fragment, peptide, or others. NPs are synthesized separately from a suitable isotope and then conjugated to biological molecules by using procedures similar to those for chelates. For example, terminal groups of stabilizer molecules coating NPs can be chemically modified to p-isothiocyanotobenzyl derivatives, which can be coupled to $NH_2$ groups of lysine residues of proteins. Alternatively, NP-protein conjugates can be prepared via NP-biotin dyads (NP-B) to provide a synthetic route to preparation of heterogeneous conjugates combining two different bioactive moity. The new radiopharmaceuticals substantially improve the clinical properties of currently used radiolabeled compounds for the following reasons:

(1) The dissociation constants, K, for chelates are many orders higher than that of metal sulfides of clinical interest: logK for the strongest chelates is known to be >−30, while $logK(In_2S_3)=-73.24$, $logK(CuS)=-35.2$, $logK(Bi_2S_3)=-97$, $logK(Ag_2S)=-49.7$. When a radioactive metal is present in the body in the form of virtually insoluble largely covalent sulfide cluster, the formation of metal ions leading to transchelation by natural proteins is practically eliminated. Thus, the biodistribution of a radioactive material will not be compromised by the loss of chelated ion while in circulation.

(2) Numerous stabilizer molecules coating nanoparticles permit for several identical covalent bridges to be formed in one conjugation step making the overall stability of the conjugate substantially higher.

(3) Replacement of a metal complex with nanoparticles, which can be prepared for 10–20 min, eliminates long and expensive multistep procedure of chelate synthesis. Since inorganic core is much more tolerant to experimental conditions than elaborate organic molecules, surface activation and modification, should it be necessary, can be carried out as a one-pot synthesis without involvement of protective groups.

(4) Availability of multiple attachment points on the surface of nanoparticles enables design and preparation of radioimmunoconjugates with multiple targeting molecules. This will increase the uptake of the labeled compound by the cancerous cells and will promote a more uniform distribution of the drug within the tumor tissue. Conjugates of this type are currently unavailable by chelate labeling technique owing to complexity of the procedure and relatively short life-time of radionuclides.

Accordingly, application of nanoparticle/protein conjugates should significantly improve the detection limit of cancer, increase effectiveness of radiotherapy and reduce the overall radiation toxicity. Practical benefits of introducing nanoparticles in nuclear medicine also include the possibility of using low activity isotope sources. Since each nanoparticle contains 100–10,000 metal atoms, high radioisotope enrichment of the original stock solution is not required.

A better understanding of the present invention, its several aspects, and its objects and advantages will become apparent to those skilled in the art from the following detailed description, taken in conjunction with the attached drawings, wherein there is shown and described the preferred embodiment of the invention, simply by way of illustration of the best mode contemplated for carrying out the invention.

DETAILED DESCRIPTION OF THE PREFERRED EMBODIMENT

Before explaining the present invention in detail, it is important to understand that the invention is not limited in its application to the details of the construction illustrated and the steps described herein. The invention is capable of other embodiments and of being practiced or carried out in a variety of ways. It is to be understood that the phraseology and terminology employed herein is for the purpose of description and not of limitation.

Properties of nanoparticles of metals were first predicted by theoretical work by L. Brus on the basis of quantum mechanical calculations. See Brus, L., Radiationless Transitions in Cdse Quantum Crystallites, *Is. J. Chem.*, 1993, 33, 15 and references therein (incorporated by reference). It was found that the absorption spectra of semiconductor particles with the size of 1–10 nm is supposed to strongly depend on their diameter. Experimentally they were first observed by A. Heinglein and M. Gratzel, who confirmed the predictions. See A. Henglein, Small-particle Research: Physicochemical Properties of Extremely Small Colloidal Metal and Semiconductor Particles, *Chem. Rev.*, 1989, 89, 1861. and B. O'Regan and M. Gratzel, a Low Cost, High Efficiency Solar Cell Based on Dye-sensitized Colloidal $TiO_2$ Films, *Nature*, 1991, 353, 737 and references therein (both incorporated by reference). After that optical and electronic properties of semiconductor nanoparticles and particularly metal sulfides were in the focus of many scientists.

Typically, NPs are synthesized by arrested precipitation in the presence of thiols. For all thiols, —SH end forms a strong bond with surface atoms of a metal while the opposite end the stabilizer can carry various functional groups suitable for further derivatization. The NPs obtained following this general recipe can be represented by an approximate model in FIG. 1.

One aspect of the present invention involves the synthesis of nanoparticles easily redispersible in water. The later requirement is necessary for future conjugation to proteins which do not tolerate hydrophobic media. In connection with the present invention there is provided a relatively uniform method for the synthesis of $ReS_2$, $Ag_2S$ and $In_2S_3$ nanoparticles.

When a radioconjugate is administered for the purpose of cancer therapy, the portion of gamma-quanta in gamma-emitting nuclides should be minimized to avoid unnecessary whole body irradiation. Among many other perspective radionuclides $^{111}Ag$ and $^{186}Re$ have the lowest abundance of gamma-radiation: 7% and 16% respectively [Schubiger, A. P. et al. *Bioconjugate Chem.*, 1996, 7 (2), 165–179]. Unfortunately, low chemical stability of corresponding chelates causes serious practical problems for both metals. Silver nuclides are particularly exemplary in this respect. Despite favorable emission properties, $^{111}Ag$ has not been viewed favorably in nuclear medicine because of high lability of the metal center. Stability constants rarely exceed 1000, and the highest constant described for an 18-membered $N_2S_4$ system was 1014 [Craig, A. S. et al. *J. Chem. Soc., Perkin Trans.*, 1990, 2, 1523–1531]. It has to be considered in the latter case that this is an absolute and not a conditional constant. This means that the amines in the multidentate chelate will be protonated in physiological solution, with the conditional constants being therefore much lower. The stability constant for silver sulfide is $5 \cdot 10^{49}$ and $Ag_2S$ nanoparticles are virtually indestructible under physiological conditions. By using the nanoparticle technology the preparation of radioimmunoconjugates with $^{111}Ag$ becomes possible.

Chelates of indium are considered to be one of the most promising and are currently undergoing clinical trials for radioscintillation imaging of cancer. Indium is also preferred for the present invention because $In_2S_3$ nanoparticles should substantially improve the performance of $^{111}In$ pharmaceuticals. The transchelation reactions will be eliminated and therefore the tumor-to-background ratio will be improved (stability constant of $In_2S_3$ is $1.7 \cdot 10^{73}$). The preparation of the conjugates will be simplified and will become more cost effective. Besides that, imaging capabilities of $^{111}In$ suffer from its rather short half-live, $t_{1/2}=67$ hours. Quite often the radioscintillation study has to be conducted for a few days after initial injection in order to detect metastases. Although $t_{1/2}$ cannot be changed, but the actual contrast of the image will be substantially improved for NP conjugates as compared to chelates particularly for period of time longer than $t_{1/2}$ has passed due to the greater number of $^{111}In$ nuclei per conjugate retaining their activity. Improvement of targeting and blood clearance times can also be achieved via attachment of several tumor-seeking biological molecules to one radiolabel, which is quite complicated synthetically for $^{111}In$-chelates. NPs of silver, indium, rhenium, copper and other sulfides can be synthesized by arrested precipitation in the presence of thiols. For all thiols, —SH end forms a strong bond with surface atoms of a metal while the opposite end the stabilizer can carry various functional groups suitable for further derivatization. Synthesis of NPs is preferably accomplished as exemplified here for rhenium sulfide nanoparticles and indium sulfide nanoparticles.

EXAMPLE 1

50 mg $ReCl_5$ ($1.38 \times 10^{-4}$ moles) and 0.02 ml of thioglycerol ($1.38 \times 10^{-4}$ moles) are dissolved in 15 ml of DMF. The reaction mixture is purged with nitrogen to get rid of dissolved oxygen and 2.75 ml of 0.1M $Na_2S$ ($2.751 \times 10^{-4}$ moles) are injected in vigorously stirred solution. Initially transparent colorless mixture becomes intensively brown, which indicates formation of nanoparticles. Nanoparticles can be separated from the liquid phase by adding 1:1 volume of acetone. After centrifugation, the dark solid washed with ethanol and dried. For further modifications $ReS_2$ nanoparticles can be redispersed in water, DMF, DMSO and other polar solvents.

EXAMPLE 2

50 mg of $InCl_3$ and 0.18 ml of thioglycerol, TG, (or 32 mg of 1-amino-2-methyl-2-propanethiol hydrochloride, AMPT) are dissolved in 20 ml of deoxygenated water ($N_2$, bubbling for 20 minutes). The molar concentration of stabilizer is ten times that of the metal. This mixture is vigorously stirred and 3.39 ml of 0.1M aqueous solution of sodium sulfide was added. Indium sulfide nanoparticles in the solution were sedimented from the mother liquor by isopropanol as a white powder, that can be used in subsequent modification reactions.

The size of nanoparticles can be controlled by several means: (1) addition of a solvent with lower electron donor capacity ($CH_3OH$), (2) reduction the stabilizer/metal molar ratio; or (3) increase of the temperature of the solution during addition of $S^{2-}$. It is preferred to work with nanoparticles of 1–3 nm in diameter, which are regularly obtained under ambient conditions.

The size of the nanoparticle clusters can be readily assessed by transmission electron microscopy (TEM) and by using UV-absorption spectrophotometry. The peak in UV-absorption strongly depends of the particle diameter: for CdS the peak shifts from 250 nm to 480 nm when the diameter on the nanoparticles increases from 14 Å to 100 Å. Emission properties of nanoparticles change according to their diameter as well. However, there is a strong influence of the emission spectrum of nanoparticles on surface conditions, and, therefore, the usage of absorption characteristics for size estimate is preferential.

Figure 1:
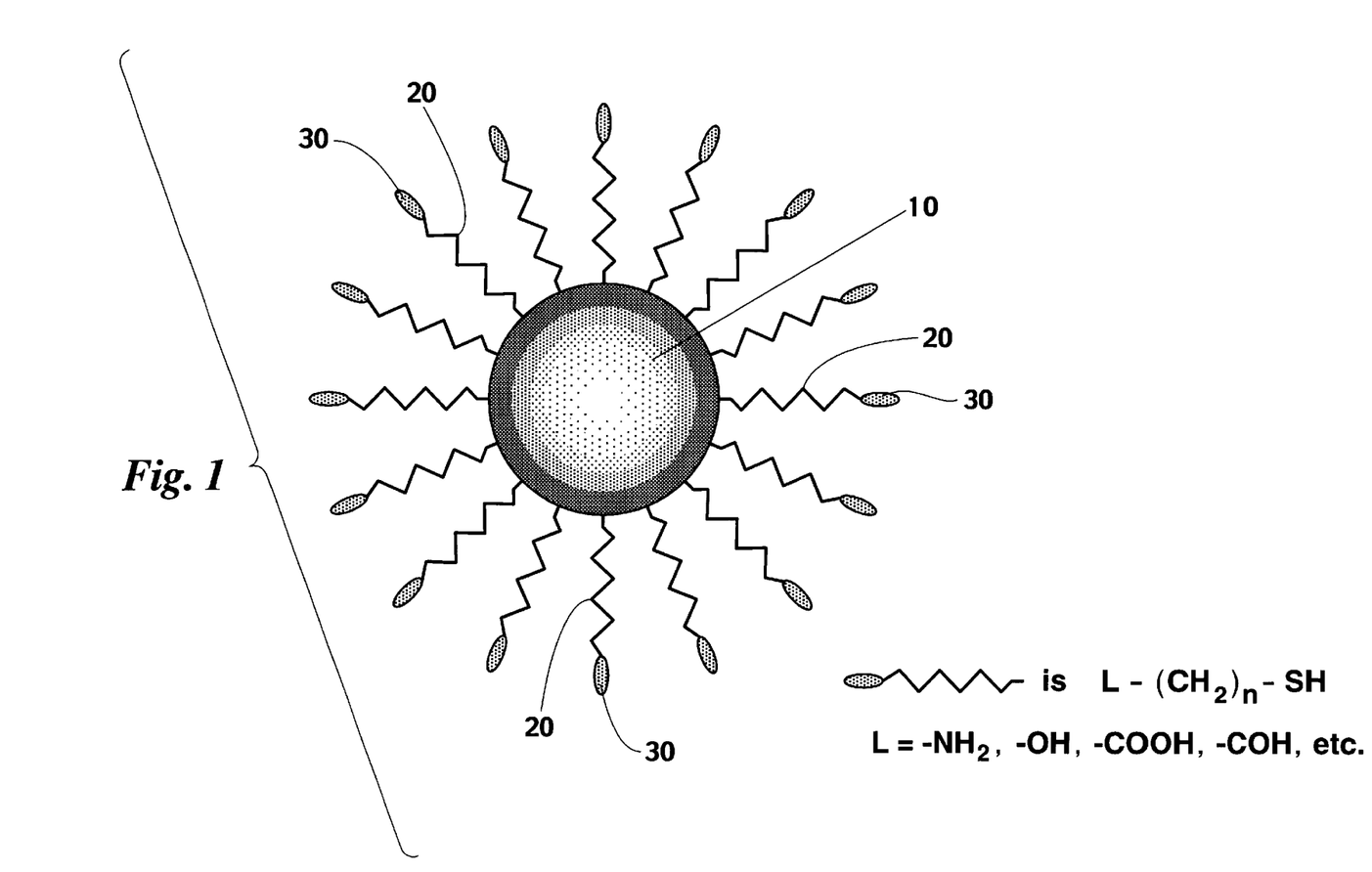
FIG. 1 is a schematic of a nanoparticle surrounded by a stabilizer with a functional terminal group.

Referring to FIG. 1, the surface of the NP 10 is inherently functionalized by chemical groups 30 present in thiol stabilizers. Thiolate chemistry enables using various derivatives without significant alteration of the preparation procedure of nanoparticles. There is a substantial variety of commercially available thiols with —OH, —SH, —COOH, and —$NH_2$ functional groups. The stabilizers that are currently preferred for preparation of nanoparticles include thioglycerol (—OH), mercaptosuccinic acid (—COOH), thioglycolic acid (—COOH), and 1-amino-2-methyl-2-propanethiol (—$NH_2$) (the terminal functional is group is indicated in parenthesis). The selection of a specific terminal functional group L, 20 in FIG. 1, is governed by the conjugation reactions planned for the nanoparticle. Should it be necessity to vary the stabilizer structure, for instance the hydrocarbon chain length, one can synthesize the compound series by using classical methods of organic chemistry.

Changes occurring with the organic shell around the nanoparticle may be monitored using methods such as: fluorescence spectroscopy, UV-VIS absorption spectroscopy, Fourier transform infrared spectroscopy (FTIR), Raman spectroscopy, and nuclear magnetic resonance (NMR). These methods can be use to generate multifaceted characterization of the layer of stabilizer by probing optical vibrational, and magnetic properties of σ— and π—bonds.

Binding of the stabilizer to the NP surface significantly alters the proton and carbon signals in the vicinity of the interface. Therefore, assignment of the signals may be made in the analysis of NMR data. Two-dimensional NMR (COSY and NOESY) can be used for determination of a source of the peak as well as the environment of a selected group.

Relative intensity of $^1$H and $^{13}$C signals in functional groups is the most direct method to monitor the modification of the surface of nanoparticles. The ratio of integral intensities of NMR signatures of a protein and a nanoparticle provides the estimate of NP/protein ratio. Importantly, NMR enables evaluation of the protein conformation and, thus, its biological activity, which can be correlated with the data obtained by ELISA and immunofluorescence.

Infrared and Raman spectroscopy may be used to generate structural information to complement and augment the data obtained by NMR. The extent of surface modification of NPs may be detected by using the intensity of vibrational bands of —OH, —NH$_2$, —COOH, C=O, C—NH and other functional groups involved in the reaction.

Imaging of NP-protein conjugates using transmission electron microscopy (TEM) may be performed after staining the organic part by uranium or osmium salts to increase the contrast. Nanoparticles of the proposed metal sulfides can be readily found in TEM pictures without any additional procedures. TEM of the conjugates provides information about distribution of the NPs along the protein chain and possible crosslinking processes.

Preparation of bioconjugates of NPs can be accomplished by using standard biochemical procedures. Aromatic p-isothiocyanato group has been extensively employed to efficiently couple chelates, fluorescence probes, boron clusters or spin labels to proteins and therefore can be used for nanoparticles. p-Isothiocyanotobenzyl moiety targets —NH$_2$ functional groups in lysin aminoacid residues (FIG. 2 wherein 1 represents the nanoparticle and 2 represents the residue). Quite often they do not play a critical role in the biological activity of a protein and located in open parts of the globule. Lys and, to a lesser extent, Cys aminoacids are the targets for thiazolidine-2-thione and succinimidyl linkers. Nanoparticles terminated with hydroxyls are particularly suitable for this conjugation. A cyanuric acid condensation product, 4,6-dichloro-1,3,5-triazin-2-ylamino group, provides an alternative, more reactive and more hydrophilic [34] conjugates than p-isothiocyanotobenzyl linker. Because of its reactivity, it can be used for labeling of other amino acid residues besides lysine and even labeling of sugars. The high reactivity can also be a disadvantage. A number of monoclonal antibodies lose easily their affinity when conjugated with 4,6-dichloro-1,3,5-triazin-2-ylamino-activated chelate.

Figure 2:
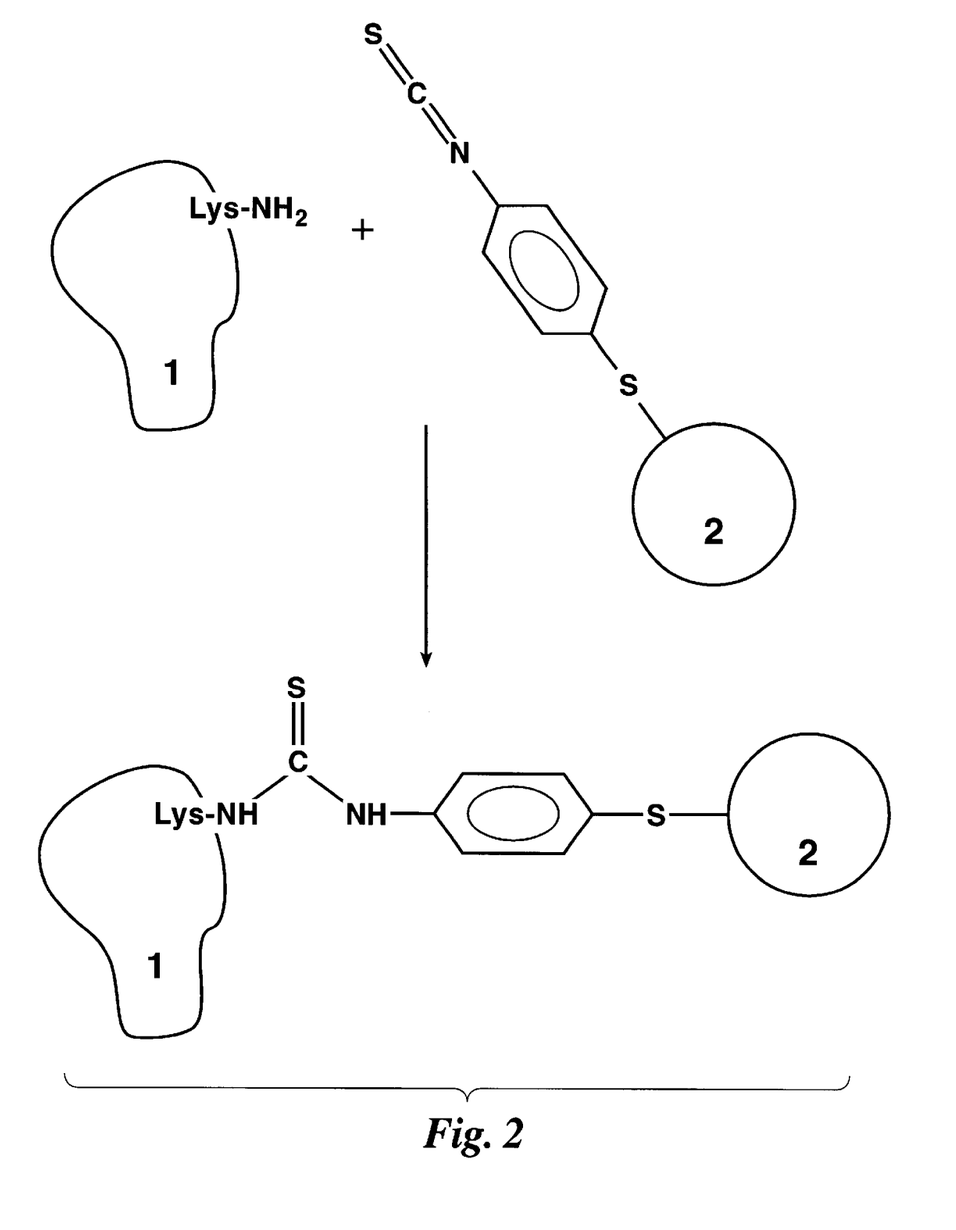
FIG. 2 is a schematic example of a conjugation reaction between functionalized nanoparticles and a protein.

In connection with the present invention, the p-isothiocyanotobenzyl group was selected for preparation of the first examples of NP-protein conjugates due to simplicity and mild and efficient coupling to proteins (FIG. 2). In perspective this method appears to be well suitable for the preparation of mAbs conjugates and radiopharmaceuticals. One can use two alternative routes to produce SCN—C$_6$H$_4$—derivatized metal sulfide nanoparticles. Both of them are quite universal in respect to the type of metal sulfide NPs being attached. The first protocol involves an intermediate activation step and offers variable degree of conjugation. In a series of preliminary experiments it was demonstrated that p-thioaniline (HS—C$_6$H$_4$—NH$_2$) is efficient stabilizer for PbS, ReS$_2$ and In$_2$S$_3$ nanoparticles. Their surface derivatized with —S—C$_6$H$_4$—NH$_2$ groups is a convenient precursor for generation of —C$_6$H$_4$—NCS.

Classical reaction with thiophosgene results in the conversion of NP—S—C$_6$H$_4$—NH$_2$ to NP—S—C$_6$H$_4$—NCS. Thiophosgene is not soluble in water and is normally used in the form of chloroform solution. Conversely, NPs are rather hydrophilic. Nevertheless, finding a common solvent for these two reagents is not required since the modification reaction is quite efficient at the interface of CHCl$_3$ and a basic aqueous solution (pH=8.5) forming unstable emulsion upon stirring. The average number of —C$_6$H$_4$—NCS groups per nanoparticles can be controlled via the overall reaction time and amount of thiophosgene. A mixture of two stabilizers may also be used for the preparation of nanoparticles, for instance, HS—C$_6$H$_4$—NH$_2$ and thioglycerol terminated by fairly inactive —OH groups. In this case, only —S—C$_6$H$_4$—NH$_2$ moieties will be derivatized by thiophosgene. The ratio between the two stabilizers can be adjusted so that 1–2 reactive p-isothiocyanato groups per nanoparticle are produced. This will ensure a better control over the NP-protein conjugate and will minimize possible adverse effects on protein activity.

To speed up the procedure of preparation of labeled compounds—an important requirement when working with short half-life radionuclides—one can use a p-isothiocyanato bearing thiol, HS—CH$_2$—C$_6$H$_4$—NCS from the beginning of the nanoparticle synthesis as a stabilizer. This will produce labels suitable for conjugation to proteins within a 10–15 minutes after obtaining a radionuclide as compared to a typical chelating procedure which requires several hours to incorporate a metal ion into the macrocyclic cage.

Controlled ratio of different moieties coating NP can be achieved by variation of the ratio of stabilizers in the reaction mixture for NP preparation. Since each nanoparticle bears a substantial number of stabilizing groups (>10) on its surface, the statistical distribution will reflect quite accurately the concentrations of the corresponding molecules and their relative reactivity toward binding to a growing metal sulfide cluster. Detection of the number of reactive groups per nanoparticle can be achieved by spectroscopic techniques.

It is necessary to mention that, very fine degree of control over the number of reactive groups on the surface of nanoparticles is desirable but not a mandatory prerequisite for the preparation of radioimmunoconjugates. Assuming quite a broad distribution of reactive groups per nanoparticle—the number of —(CH$_2$)$_n$—C$_6$H$_4$—NCS moieties varies between 1 and 5. The product of coupling to a protein may contain both crosslinked products and unreacted —(CH$_2$)$_n$—C$_6$H$_4$—NCS groups. The latter can be easily quenched by addition of a lysine or a low molecular weight amine. As to the crosslinked species, they can be readily separated by centrifugation.

The activity of all proteins after conjugation can be established by ELISA, registering the kinetics of the color development (formation of purpurogallin from pyrogallol at pH=6.0 at 20° C.). The molecular weight of the conjugates may be estimated initially by silver stain SDS-PAGE and by mass spectroscopy with electrospray ionization (other ionization methods have proven to damage both nanoparticles and proteins).

Stability of the conjugates can be assessed by incubation with transferrin and excess of albumin at 37° C. for several hours in dark (the nanoparticles are likely to be light sensitive). The pH of the solution may be varied between 8.0 and 4.0 to cover most of the biologically relevant pH conditions. The products can be separated by affinity chromatography and the fractions collected and analyzed by atomic ionization spectroscopy for the presence of the radiolabel. Incubation in human serum may also be used for more rigorous stability characterization. The extent of transchelation can be evaluated by the amount of a ionized form of metal assessed spectroscopically and electrochemically after chromatographic separation of the fraction with nanoparticles.

Any heterogeneous conjugates constructed can be fractionated by chromatography and analyzed by ELISA, immunofluorescence and SDS-PAGE in order to establish the presence of two distinct biological moieties attached to one NP. An example of an advanced conjugate consisting of two different biological moieties can be constructed using biotin (vitamin H) and streptavidin (Mw=60,000). Numerous biotinylated proteins are widely available commercially. Biotinylated horseradish peroxidaze may be employed for easy detection in the corresponding constructs. F(ab=)$_2$ fragment of antibody to rabbit IgG including its FTIC-labeled analog may be used when antibody fragments rather than a whole antibody is desirable. Folic acid and small peptides such as somatostatin (Ala-Gly-Cys-Lys-Asn-Phe-Phe-Trp-Lys-Thr-Phe-Thr-Ser-Cys) with distinct affinity to cancer cells are to be considered as within the scope of this invention for conjugation to nanoparticles as well.

A staggeringly large value of binding constant for non-covalent interaction between biotin (B) and avidin or streptavidin (SA), logK=15, and four independent docking spots make biotin technology an important pathway to preparation of various conjugated systems. A large variety of biotinylated proteins, antibodies and peptides is commercially produced. The biotin-streptavidin link renders the preparation of various conjugates simple and quite universal.

Figure 3:
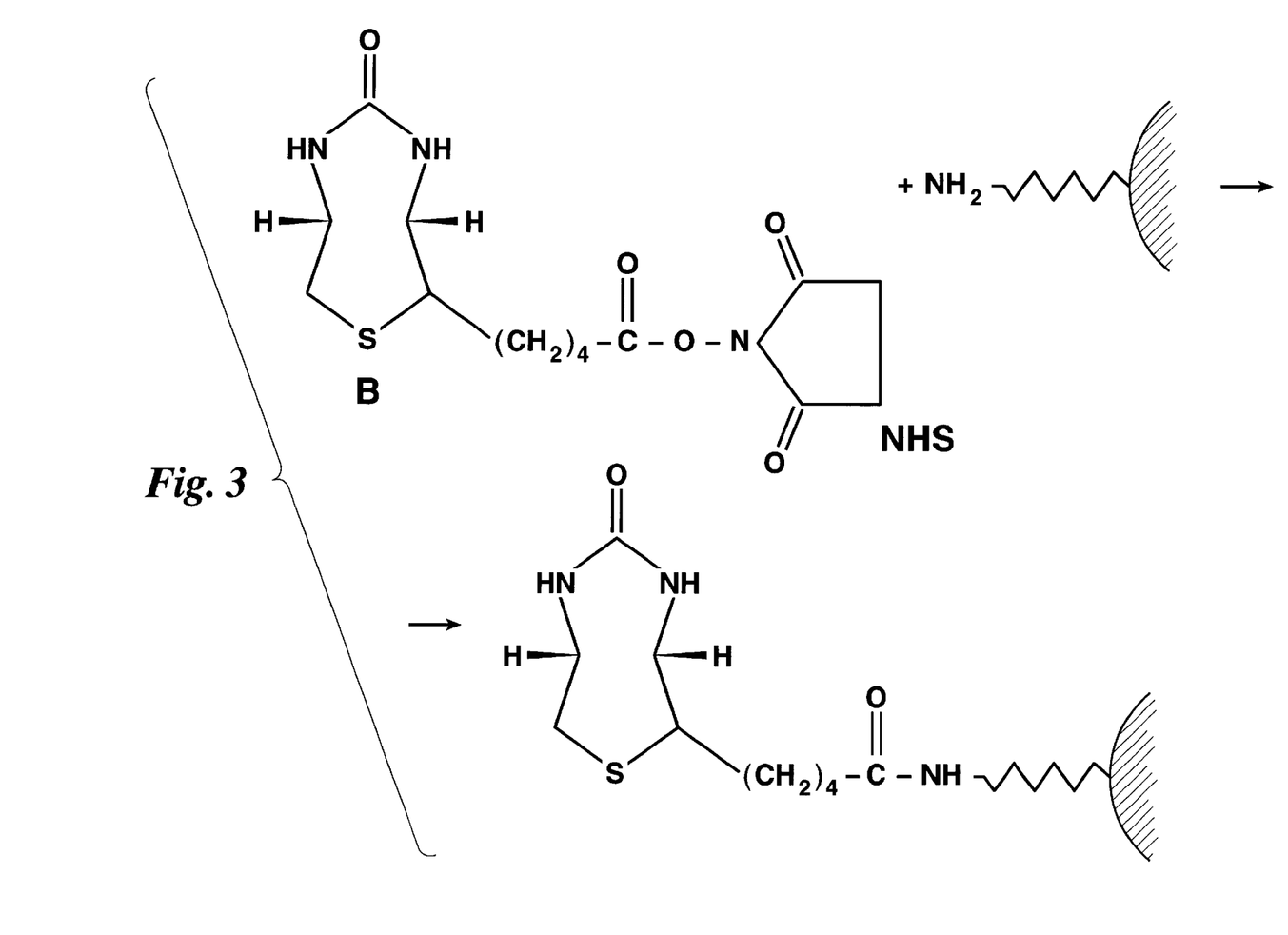
FIG. 3 is a schematic illustrating the preparation of biotine-modified nanoparticles.

Streptavidin derivative of NPs can be prepared following the procedure outlined above. Biotinylation of NPs can be accomplished by a number of ways via attachment to amine, aldehyde, carboxyl, thiol and phenol functional groups located on nanoparticle. For previously mentioned —S—(CH$_2$)$_n$—NH$_2$ stabilizer, N-hydroxysuccinimide (NHS) ester of biotin (B-NHS) can be a convenient conjugation agent (FIG. 3). A typical nanoparticle biotynilation procedure can be the following.

EXAMPLE 3

Nanoparticles are dissolved in 0.1 M NaHCO$_3$ aqueous solution at a concentration 2–5 mg/ml. An appropriate volume of 2–10 mg/ml solution of biotin-NHS is added to obtain biotin-NHS to nanoparticles ratios 0, 2, 5, 10, 20, and 50. Each reaction mixture is allowed to stand for 2 hr at room temperature. The samples are extensively dialyzed against pure water.

EXAMPLE 4

For an example of NP-protein conjugates, reference is made to a simple conjugation reaction between NP stabilized with a thiol bearing —NH$_2$ groups, bovine serum albumin (BSA) and glutaroaldehyde (G). Carboxyl groups on both ends of G react with amino groups of both nanoparticles and BSA, thereby establishing a link between them made of strong covalent bonds. The reaction proceeds at room or slightly elevated temperature (45° C.) for one hour, which preserves the biological activity of the protein. Gel electrophoresis experiments of the conjugates revealed that virtually all NPs are bound to the protein. This conjugation technique is particularly attractive due to its simplicity, speed and mild, efficient coupling to proteins. In perspective this method is well suited for the preparation of mAbs conjugates and radiopharmaceuticals.

Similarly to proteins, a nanoparticle can accommodate several biotin moieties. These isomers can be easily separated by affinity chromatography on modified Sepharose. The actual number of B-groups per metal sulfide cluster can be determined spectroscopically (NMR, MS) and by classical colorimetric method based on the displacement of the dye 4-hydroxyazobenzene-2-carboxylic acid (HABA) from the binding sites of avidin [39]. HABA binds to avidin to give an absorption maximum at 500 nm. When biotin or biotinylated species are added, biotin displaces HABA from avidin and the absorbency at 500 nm is reduced. The decrease in absorbency is then used to determine the extent of biotinylation. Preparation of NPs with 1,2,3,4 etc. biotin groups on the surface opens unique possibilities for molecular engineering of nanoparticles and creation of superstructures on their basis.

Long-chain derivatives, which can be produced by introducing N-ε-aminocaproic acid link between B and NHS, are somewhat preferential over a short connection obtained by condensation-NH$_2$ and —NHS due to better steric position of the biotin group for subsequent docking to streptavidin. These conjugates are easier to hydrolyze and, therefore, are likely to compromise in-vivo stability of radioconjugates from Nps.

Advanced conjugates are also within the scope of the present invention. Intact antibodies possess higher affinity to cancer but have long blood clearance time. Additionally, the whole mAbs are more immunogenic than their fragments. On the other hand F(ab=) and F(ab')$_2$ having a lower molecular mass of 50 kDa and 100 kDa respectively, clear the blood faster than mAb but demonstrate substantially worse T/B ratio. The hope for finding a solution to this dilemma has been recently offered in a series of works on chemically constructed assemblies of antibody fragments such as F(ab')$_2$, F(ab')$_3$, and F(ab')$_4$. Tumor uptake for these assemblies was 2–2.5 times higher than for normal F(ab')$_2$ and similar to that observed with the intact mAb. For some of them accumulation in kidney or liver was greatly reduced. Thus, chemically engineered immunopharmaceuticals are envisioned to be a viable alternative to whole mAbs.

Small peptides (somatostatin and its analogs), folic acid, bleomycin and other low molecular weight compounds with distinct tendency to accumulate in cancer cells should also be considered within the scope of this invention for creation of similar radiolabeled constructs. Particularly preferred is the combination of two different target moieties on one radiolabel, for instance mAb+peptide or somatostatin+F(ab')$_2$. Engaging diverse adsorption mechanisms will increase the overall tumor uptake and will improve the distribution of "hot" particles in the target since different tumor-seeking agents have different sites of preferential adsorption within cancer tissue.

Nanoparticles with multiple bonding points appear to be well suited for preparation of "designer antibodies". Homogeneous assemblies such as F(ab')$_4$ can be prepared via extensive activation of the nanoparticle surface followed by the conjugation to F(ab')$_2$ fragments. After formation of the desired aggregates unreacted aromatic p-isothiocyanato groups can be quenched by lysine. Depending on the length of the stabilizer and diameter of NP, two or three F(ab')$_2$ units are likely to get attached. The actual number of antibody fragments per NP can be determined by TEM and by SDS-PAGE.

Heterogeneous constructs containing two different moieties can be prepared by using NP-biotin derivatives described above. A nanoparticle containing both —NH$_2$ groups and at least one biotin moiety can be conjugated to a monoclonal antibody or a small peptide via regular techniques by using —NH$_2$ activation leaving the biotin group intact. The second part, for example, mAb, F(ab') will be appended via streptavidin linker. This method is likely to produce isomers due to multiple docking sites on streptavidin. However they can be readily separated due to large difference in molecular weight and size by using size exclusion chromatography.

As thus described there is provided exceptionally stable metal sulfide nanoparticles for replacing metal chelates in radioimmunoconjugates. Virtual elimination of ionic radioactive species will improve the performance of radiolabeled compounds and decrease radiation damage to healthy tissue. As well, radioactive nanoparticles will simplify the preparation procedure, decrease the cost, and open new possibilities for the creation of molecularly designed immunochemicals.

While the invention has been described with a certain degree of particularity, it is understood that the invention is not limited to the embodiment(s) set for herein for purposes of exemplification, but is to be limited only by the scope of the attached claim or claims, including the full range of equivalency to which each element thereof is entitled.

What is claimed is:

1. A bioconjugate, comprising: a radioactive, metal sulfide or metal oxide nanoparticle covalently linked to at least one biological vector molecule.

2. The bioconjugate of claim 1 wherein said at least one biological vector molecule is selected from a group consisting of monoclonal antibodies (mAb), fragments of monoclonal antibodies, and peptides.

3. The bioconjugate of claim 1 wherein the nanoparticle is a metal sulfide selected from a group consisting of Ag$_2$S, PbS, CdS, In$_2$S, CuS, Bi$_2$S$_3$ and ReS$_2$.

4. The bioconjugate of claim 1 wherein the nanoparticle is titanium oxide.

5. The bioconjugate of claim 1, wherein the nanoparticle is surface stabilized by a molecule or molecules having a thiol functional group.

6. The bioconjugate of claim 5 wherein the thiol functional group is selected from a group consisting of thioglycerol, mercaptosuccinic acid, thioglycolic acid, and 1-amino-2-methyl-2-propanethiol.

7. The bioconjugate of claim 1 wherein the nanoparticle is surface stabilized by a protein.

8. The bioconjugate of claim 1 wherein the nanoparticle has a diameter between approximately 1 and 10 nm.

9. The bioconjugate of claim 8 wherein the diameter of the nanoparticle is between 2 and 5 nm.

10. The bioconjugate of claim 1 further comprising: a second biological moiety wherein said second biological moiety is different from said biological vector molecule.

11. The bioconjugate of claim 10 wherein the second biological moiety is selected from a group consisting of biotinylated proteins, antibody fragments, folic acid, and somatostatin.

* * * * *